(12) United States Patent
Röder et al.

(10) Patent No.: US 7,297,804 B2
(45) Date of Patent: Nov. 20, 2007

(54) CATALYTIC COMPOSITION OF ORGANOTIN COMPOUNDS

(75) Inventors: Jens Röder, Frankfurt am Main (DE); Andrea Kapries, Herbern (DE); Liane Franke, Datteln (DE); Oliver Schumacher, Werne (DE); Johannes Canisius, Bochum (DE)

(73) Assignee: Chemtura Organometalics GmbH, Bergamen (DE)

( * ) Notice: Subject to any disclaimer, the term of this patent is extended or adjusted under 35 U.S.C. 154(b) by 120 days.

(21) Appl. No.: 10/536,658

(22) PCT Filed: Nov. 25, 2003

(86) PCT No.: PCT/EP03/13221

§ 371 (c)(1), (2), (4) Date: May 27, 2005

(87) PCT Pub. No.: WO2004/050742

PCT Pub. Date: Jun. 17, 2004

(65) Prior Publication Data

US 2006/0047101 A1     Mar. 2, 2006

(30) Foreign Application Priority Data

Nov. 29, 2002   (DE) ................................ 102 56 084

(51) Int. Cl.
*C07F 5/00*   (2006.01)
*C08G 63/02*   (2006.01)

(52) U.S. Cl. ........................................ 556/1; 528/272
(58) Field of Classification Search ............... 556/1
See application file for complete search history.

(56) References Cited

U.S. PATENT DOCUMENTS

| | | |
|---|---|---|
| 4,014,858 A | 3/1977 | Chipman et al. |
| 4,064,112 A | 12/1977 | Rothe et al. |
| 4,263,425 A | 4/1981 | Rothe et al. |
| 5,362,844 A | 11/1994 | Kerpes et al. |
| 5,419,936 A * | 5/1995 | Tindale ............. 428/35.8 |
| 5,663,281 A | 9/1997 | Brugel |
| 6,114,496 A | 9/2000 | Otera et al. |

OTHER PUBLICATIONS

Dakternieks et al. "Synthesis, structure and reactions of [(BuSn)$_{12}$O$_{14}$(OH)$_6$]Cl$_2$ 2H$_2$O: solution studies using $^{119}$Sn NMR and electrospray mass spectrometry", *Journal of Organometallic Chemistry*, 476 (1994) 33-40.

Durand et al. "Cationic Organotin Clusters for Highly Efficient Alcohol Acetylation Catalysts", *Organometallics*, 2000 (19) 3220-3223.

Fakirov, Handbook of Thermoplastic Polyers, "Homopolymers, Copolymers, Blends and Composites" 2002, vol. 1.

Johnson, et al. "World fiber demand 1890-2050 by main fiber type", *Chemical Fibers International*, 46 (1996) 280-286; 49 (1999).

Puff, et al. "Zur Hydrolyse von Monoorganylzinn-trihalogeniden", *Journal of Organometallic Chemistry*, 373 (1989) 173-184.

Johnston, et al. "Ou tlook for Man-Made Fibers to 2005/2010", *Chemical Fibers International*, 49 (1999) 455-459.

* cited by examiner

*Primary Examiner*—Yvonne Eyler
*Assistant Examiner*—M Louisa Lao
(74) *Attorney, Agent, or Firm*—Daniel Reitenbach

(57) ABSTRACT

The present invention relates to catalytic compositions for esterification, transestrification and polycondensation reactions, a process for the catalysis of said reactions employing such catalytic compositions and polyesters for resins obtainable by this process.

17 Claims, No Drawings

CATALYTIC COMPOSITION OF ORGANOTIN COMPOUNDS

BACKGROUND OF INVENTION

The present invention relates to catalytic compositions for esterification, transesterification and polycondensation reactions, a process for the catalysis of said reactions employing such catalytic compositions and polyesters or resins obtainable by this process.

Catalytic systems containing organotin compounds are widely known.

E.g. compounds of the formula $[(RSn)_{12}O_{14}(OH)_6]^{2+}$ are described mainly in connection with their interesting structure in: H. Puff, H. Reuter, J. Organomet. Chem. 1989, 373, 173-184; D. Dakternieks, H. Zhu, E. R. T. Tiekink, R. Colton, J. Organomet. Chem. 1994, 476, 33-40; S. Durand, K. Sakamoto, T. Fukuyama, A. Orita, J. Otera, A. Duthie, D. Dakternieks, M. Schulte, K. Jurkschat, Organometallics 2000, 19, 3220-3223.

Compounds of said type $[(RSn)_{12}O_{14}(OH)_6]^{2+}$ are further described to show a poor performance in catalyzing or activating reagents and compounds within the acetylation reaction of acetic anhydride with an alcohol (S. Durand, K. Sakamoto, T. Fukuyama, A. Orita, J. Otera, A. Duthie, D. Dakternieks, M. Schulte, K. Jurkschat, Organometallics 2000, 19, 3220-3223.)

It is known for compounds of the formula $[(BuSn)_{12}O_{14}(OH)_6]^{2+}$ when stored in methanol, that a replacement of two structural important µ2-bridged OH groups of the cluster against $OCH_3$ units can occur (D. Dakternieks, H. Zhu, E. R. T. Tiekink, R. Colton, J. Organomet. Chem. 1994, 476, 33-40).

Furthermore is known that during the production of polyesters for some applications for example wrappings and technical yarns, a crystallization and polycondensation in the solid state is carried out (U.S. Pat. No. 4,064,112, U.S. Pat. No. 4,263,425, U.S. Pat. No. 5,362,844). In other applications, fibers or filaments are spun directly and direct preforms are produced in a process wherein an intermediate transfer into the solid state and a repeated remelting is not applied.

Conventional polyester compositions are connected with a series of disadvantages (general summary in: Handbook of polyester thermoplastics, 1st edition, Wiley-VCH, Weinheim, 2002). Among these disadvantages are in particular:

Necessity of high temperatures for the synthesis
High catalyst concentration (100-500 ppm [as metal])
Degradation processes under processing and polycondensation conditions; for example formation of vinyl esters and due to the formation of acetic aldehyde in polyethylene terephthalate (PET), formation of acrolein in polypropylene terephthalate (PPT) and tetrahydrofuran formation in polybutylene terephthalate (PBT).
Limited use of the catalyst systems, dependent on the technology of the process and the chemical structure of the substrate; classic titanium based catalysts cannot be added for example during the esterification- and/or pre/condensation step, as these are readily hydrolyzed to inactivate titanium oxides.
Application of the catalyst system only in selected process stages for example only during the esterifications- or only during the transesterification- or only during the polycondensation stage.
Optical turbidity of the produced polyester for example by deposits of elementary metal impurities as this can occur by the use of antimony based catalyst systems.
Discoloration of the polyester by the catalyst itself, for example titanium based catalyst systems cause a yellow coloring of the polymer or formation of chromophor by-products, respectively.
Problematic metering and addition of catalysts and catalyst formulations.

SUMMARY OF THE INVENTION

Object of the present invention is to provide a catalytic composition, suitable for catalyzing esterification, transesterification and polycondensation reactions, an improved process of catalyzed esterification, transesterification and polycondensation reactions and the production of improved polyesters for bottles, films, foils, yarn, molded padding, resins for powder coatings and technical synthetic materials, which avoid the disadvantages of the prior art.

The problem is solved according to the invention by a catalytic composition, a process for the preparation of such catalytic compositions, their use and polyesters or resins as described herein.

DESCRIPTION OF THE PREFERRED EMBODIMENTS

A first embodiment of the present invention refers to a catalytic composition for esterification, transesterification and polycondensation reactions of dicarboxylic acids, polycarboxylic acids, hydroxy carboxylic acids and/or their derivatives and alcohols containing at least one tin compound of the general formula (I):

$$[(R^1Sn)_l(OH)_{m-n}(OR^2)_nO_o]^{p+} A^{q-}_{p/q} \quad \text{(formula I)}$$

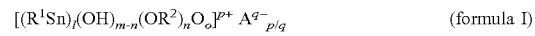

wherein:

$R^1$ and $R^2$ each independently is a linear, branched or cyclic alkyl group or aryl group having 1 to 12 carbon atoms,
$A^{q-}$ is an anion,
l is at least 1,
m=0 to 20,
n=0 to 20,
p=0 to 6,
o=0 to 20 and
q=0 to 6.

Preferred examples for $R^1$ are methyl, ethyl, n-propyl, iso-propyl, n-butyl, 2-butyl, iso-butyl, tert-butyl, n-pentyl, iso-pentyl, neo pentyl radical, tert-pentyl, hexyl, heptyl, n-octyl, iso-octyl, 2-ethyl-1-hexyl, 2,2,4-trimethylpentyl, nonyl, decyl, dodecyl, n-dodecyl, cyclopentyl, cyclohexyl, cycloheptyl, methylcyclohexyl, vinyl, 1-propenyl, 2-propenyl, naphthyl, anthranyl, phenanthryl, o-tolyl, p-tolyl, m-tolyl, xylyl, ethyl phenyl, mesityl, phenyl, benzyl. Favored substituents for the invention are: Methyl, n-butyl, n-octyl and n-dodecyl.

Examples for $R^2$ are methyl, ethyl, n-propyl, iso-propyl, n-butyl, 2-butyl, iso-butyl, tert-butyl, n-pentyl, iso-pentyl, neo pentyl, tert-pentyl, hexyl, heptyl, n-octyl, iso-octyl, 2,2,4-trimethylpentyl, 2-hydroxy-1-ethylpentyl, hydroxy-neo-pentyl, 2-ethyl-1-hexyl, nonyl, decyl, dodecyl, n-dodecyl, cyclopentyl, cyclohexyl, cycloheptyl, methylcyclohexyl, vinyl, 1-propenyl, 2-propenyl, naphthyl, anthryl, phenanthryl, o-tolyl, p-tolyl, m-tolyl, xylyl, ethyl phenyl, mesityl, phenyl, benzyl. Favored substituents for the invention are: Methyl, ethyl, n-propyl, iso-propyl, n-butyl, 2-butyl, iso-butyl, tert-butyl.

Preferred examples for A are: O, OH, methanolate, ethanolate, n-propanolate, iso-propanolate, n-butanolate, 2-butanolate, iso-butanolate, tert-butanolate, n-pentanolate, iso-pentanolate, neo-pentanolate, tert-pentanolate, 2-methyl-1-butanolate, hexanolate, heptanolate, n-octanolate, iso-octanolate, 2,2,4-trimethylpentanolate, nonanolate, decanolate, dodecanolate, n-dodecanolate, cyclopentanolate, cyclohexanolate, cycloheptanolate, methylcyclohexanolate, glycolate, glycerate, pinakolate neopentylglycolate, vinylalkoholate, propargylalkoholate, 2-ethyl-1-hexanolate, formiate, acetate, propionate, butyrate, valeriate, caprylate, caprinate, laurate, laureate, 2-ethyl-1-hexanoate, neodecanoate, palmitate, stearate, benzoate, terephthalate, phthalate, isoterephthalate, acrylate, methacrylate, crotonate, iso-crotonate, vinylacetate, oleate, sorbate, linolate, linolenate, trifluoracetate, methansulphonate, ethanesulphonate, n-propanesulphonate, iso-propanesulphonate, n-butanesulphonate, 2-butanesulphonate, iso-butanesulphonate, tert-butanesulphonate, n-pentanesulphonate, iso-pentanesulphonate, neo-pentanesulphonate, tert-pentanesulphonate, 2-methyl-1-butanesulphonate, hexanesulphonate, heptanesulphonate, n-octanesulphonate, iso-octanesulphonate, 2,2,4-trimethylpentan sulphonate, nonansulphonate, decansulphonate, dodecanesulphonate, n-dodecanesulphonate, cyclopentanesulphonate, cyclohexane sulphonate, cycloheptanesulphonate, methylcyclohexanesulphonate p-toluolsulphonate, oxalate, malonate, succinate, glutarate, adipate, fumarate, maleinate, carboxylates of the following monoesters: methylmaleic acid monoester, ethylmaleic acid monoester, butylmaleic acid monoester, n-propylmaleic acid monoester, iso-propylmaleic acid monoester, n-butylmaleic acid monoester, 2-butylmaleic acid monoester, iso-butylmaleic acid monoester, tert-butylmaleic acid monoester, n-pentylmaleic acid monoester, iso-pentylmaleic acid monoester, neo-pentylmaleic acid monoester, tert-pentylmaleic acid monoester, 2-methyl-1-butylmaleic acid monoester, hexylmaleic acid monoester, heptylmaleic acid monoester, n-octylmaleic acid monoester, iso-octylmaleic acid monoester, 2,2,4-trimethylpentylmaleic acid monoester, nonylmaleic acid monoester, decylmaleic acid monoester, dodecylmaleic acid monoester, n-dodecylmaleic acid monoester, cyclopentylmaleic acid monoester, cyclohexylmaleic acid monoester, cycloheptylmaleic acid monoester, methylcyclohexylmaleic acid monoester, glycolmaleic acid monoester, glycerolmaleic acid monoester, pinakolmaleic acid monoester, neopentylglycolmaleic acid monoester, vinylmaleic acid monoester, propargylmaleic acid monoester and 2-ethyl-1-hexylmaleic acid monoester, citrate, lactate, tartrate, naphthenate, naphthalene-2,6-dlcarboxalate, naphthalene-1,6-dicarboxalate, F, Cl, ClO, $ClO_2$, $ClO_3$, $ClO_4$, $CO_3$, Br, J, CN, SCN, OCN, sulphate, hydrogensulphate, sulphite, hydrogensulphite, sulphide, phosphate, hydrogenphosphate, dlhydrogenphosphate, bis(2-ethyl-1-hexyl)phosphate, butylphosphate, dibutylphosphate, 3-phosphonopropionate, phenylphosphoic acid, benzylphosphoic acid, p-aminophosphoic acid, n-octylphosphoic acid. Favored substituents for the invention are: methanolate, ethanolate, n-propanolate, iso-propanolate, n-butanolate, 2-butanolate, iso-butanolate, tert-butanolate, bis(2-ethyl-1-hexyl)phosphate, neodecanoat, 2-ethylhexanoat, and 2-ethyl-1-hexylmaleic acid monoester, trifluoracetate, p-toluolsulphonate, Cl, Br, J, sulphate, hydrogen sulphate, phosphate, hydrogen phosphate and dihydrogen phosphate.

Said catalytic compositions proved highly effective in the catalysis of esterification, transesterification, polycondensation, polyesterification and polytransesterification reactions.

These derivatives of dicarboxylic acids, polycarboxylic acids and/or hydroxy carboxylic acids according to the invention include e.g. esters and halogenides, but not anhydrides.

In a preferred embodiment of the invention, said catalytic composition is characterized in that the anion $A^{q-}$ is $O^{2-}$, $-OH^-$, a linear, branched or cyclic alkyl carboxy or aryl carboxy group or linear, branched or cyclic alkoxy group each having 1 to 12 carbon atoms, the anion of a mineral acid or a metalate.

In particular, said anion $A^{q-}$ is a sulphate, sulphite, phosphate, halogenide or pseudo-halogenide, titanate, zirconate, aluminate or zincate anion.

According to a particularly preferred embodiment of the invention, said catalytic composition is characterized in that n=1 to 20.

In this case a specific structure within the $[(R^1Sn)_l(OH)_{m-n}(OR^2)_nO_o]^p+A^{q-}_{p/q}$—unit is created by introduction of 1 to 20 alkoxy groups $(OR^2)$.

Most preferred catalytic compositions according to the invention are characterized in that l=12, m=6, n=0 to 6, o=14 and p=2.

Since the chemical composition containing a tin compound according to formula I, having $R^1$=butyl, $R^2$=methyl, l=12, m=6, n=2, o=14, p=2, A=Cl, q=1, as such is known but is described to be used for different purposes than that of the present invention, the catalytic composition according to the present invention does not encompass the protection of said species as such.

According to the invention the specific structure within $[(R^1Sn)_l(OH)_{m-n}(OR^2)_nO_o]^{p+} A^{q-}_{p/q}$—unit is achieved by introduction of 1 to 20, preferably 1 to 6 alkoxy groups $(OR^2)$ into the unit $[(R^1Sn)_l(OH)_mO_o]^{p+} A^{q-}_{p/q}$—by conversion with suitable metal alkoxides (metal alcoholates).

Preferred examples for said metal alkoxides are: Li, Na, K, Rb, Mg, Ca, Sr, Ba, Sc, Ti, Zr, Hf, Zn or Al-methanolate-ethanolate, -n-propanolate, -iso-propanolate, -n-butanolate, -2-butanolate, -iso-butanolate, -tert-butanolate, -neo-pentanolate, -isopentanolate, -neo-pentanolate, -tert-pentanolate, -2-methyl-1-butanolate, -hexanolate, -heptanolate, -n-octanolate, -iso-octanolate, -2,2,4-trimethylpentanolate, -nonanolate, -decanolate, -dodecanolate, -n-dodecanolate, -cyclopentanolate, -cyclohexanolate, -cycloheptanolate, -methylcyclohexanolate, -glycolate, -glycerate, -pinakolate, -neopentylglycolate, -vinylalcoholate, -propargylalcoholate, -2-ethyl-1-hexanolate. Favored metal alcoholates are: Sodium methanolate, potassium t-butylate, aluminium methanolate-ethanolate, -n-propanolate, -iso-propanolate, -n-butanolate, -2-butanolate, -iso-butanolate, -tert-butanolate, -neo-pentanolate and -iso-pentanolate, titan tetra-butanolate.

According to the invention the conversion of the units $[(R^1Sn)_l(OH)_mO_o]^{p+} A^{q-}_{p/q}$ with a metal alkoxide is preferably carried out using said metal alkoxide in a proportion of 1:0.0001 up to 1:20 by mole, in particular 1:4 to 1:6.

It is furthermore preferred that the side products resulting from said conversion of the metal alkoxides with $[(R^1Sn)_l(OH)_mO_o]^{p+} A^{q-}_{p/q}$—units remain in the reaction mixture. These side products include e.g. metallic oxides, metal hydroxides and alkoxy metal hydroxides further to the catalytically active compounds $[(R^1Sn)_l(OH)_{m-n}(OR^2)_nO_o]^{p+}A^{q-}_{p/q}$. The side products of the metal alkoxides do not affect the activity of the desired compounds $[(R^1Sn)_l(OH)_{m-n}(OR^2)_nO_o]^{p+} A^{q-}_{p/q}$.

In a further embodiment of the invention, the catalytic composition as defined above is used for the continuous or batchwise production of esters or polycondensation products by esterification, transesterification, polyesterification or polytransesterification reaction.

Esterification, transesterification, polycondensation, polyesterification and polytransesterification reactions are catalyzed and accelerated by the catalytic compositions according to the invention. The inventors have shown that in comparison to conventional methods lesser amounts of catalyst and lesser amounts of stabilizer lead to comparable results. In addition, even high-viscous polyesters may be produced in a direct process in by far shorter reaction times. The novel catalytic composition of the invention is further resistant to hydrolysis and may be added already during the esterification phase and the precondensation phase or later as an active component.

Preferably, the catalytic composition according to the invention may be used for a polyesterification reaction of a dicarboxylic acid derivative with a mono, divalent or polyvalent alcohol.

It is particularly preferred to employ derivatives of di, or polycarboxylic acids being selected from the group of esters or halogenides.

Dicarboxylic acids (carboxylic acids, containing at least two carboxyl groups), e.g. terephthalic acid, 2,6-naphthalene dicarboxylic acid, isophthalic acid, 1,4-cyclohexanedicarboxylic acid, 1,6-naphthalene dicarboxylic acid, 4,4-bisphenyl dicarboxylic acids, adipic acid, phthalic acid, alkane dicarboxylic acids, halogen derivates of the mentioned dicarboxylic acids for example tetrabromophthalic acid, and copolymers of the mentioned dicarboxylic acids or the esters of the mentioned carboxylic acids for example dimethyl terephthalate, bis(hydroxyethyl)terephthalate, 2,6-dimethylnaphthalate, 1,6-dimethylnaphthalate and others are preferred according to the invention.

Polyvalent alcohols, such as ethylene glycol, 1,3-propane diol, 1,4-butane diol and/or 1,4-cyclohexane dimethanol, di-, triethylene glycol, polyglycols with a molecular weight below 1000 or neopentyl glycol, are preferably employed.

The catalytic compositions of the invention may further advantageously be used for the production of polyesters from hydroxycarboxylic acids such as p-hydroxybenzoic acid, salicylic acid, lactic acid, glycol acid and their co-polyesters with the dicarboxylic acids and/or diols described above.

It is also preferred to employ derivatives of hydroxycarboxylic acids being preferentially selected from esters.

Further recycled polyester material might be used as co/monomer within the scope of the invention.

The metal concentration of the catalytically effective metal compound is preferably 0.1 ppm to 1 mole-%, in particular 10 ppm to 100 ppm, most preferred 20 to 50 ppm with reference to the acid or derivative to be reacted.

The catalytic composition used for the production of polyester may be added during the period before the beginning of the esterification and/or transesterification until shortly before the end of the polycondensation, favored during the esterification and/or transesterification or before the precondensation steps of the production process.

A solvent or suspending agent can be added to the tin compound prior or during the manufacturing of the catalytic composition and/or said esterification, transesterification, polyesterification or polytransesterification reaction.

As solvents or suspending agents for the catalyst an alcohol and/or an alkane diol can be employed, favored are 1,2-ethane diol, 1,3-propane diol, 1,4-butane diol, 2,2-dimethylpropane-1,3-diol.

The solvent or suspending agent used according to the invention may be different or the same in the manufacturing of said catalytic composition and said esterification, transesterification, polyesterification or polytransesterification reaction.

A preferred solvent or suspending agent employed in the invention is being selected from the group of mono-, di- or polyvalent alcohols being reacted in said esterification, transesterification, polyesterification or polytransesterification reaction.

Further preferred solvent or suspending agents include an organic liquid that is indifferent with respect to the polyester production process. Examples for such indifferent organic liquids are alkanes, cycloalkanes or benzene derivatives such as benzene, toluene or xylenes. Moreover, water or a mixture of water with an alcohol or a polyvalent may be employed as solvent and/or suspending agent.

Further additives for a color correction such as cobalt salts or organic dyes or pigments may be added to the reaction mixture, preferably in amounts of 0.0001-5% by weight, in relation to the acid or derivative to be reacted.

The polyester available by the process using the catalytic compositions of the invention shows at least comparable qualities with respect to processibility as traditional polyesters, e.g. catalyzed with antimony. In comparison to conventional high-viscosity melt polymerisations, resins produced using the catalytic compositions described by the invention show a relatively low content of acetic aldehyde. In particular the polyesters synthesized with the process described by the invention show a narrow molecular weight distribution, a high translucency and give a polymer with a high, desired blue shift. A polymer of high viscosities, unlike the state of the art using Sb catalysts, obtained without difficulty.

The polymers, produced using catalytic compositions of the invention show a high blue shift (negative b-values; color values determined by using the CIE-Lab 100 color system with spectral reference beam color measuring instrument LUCI 100, Dr. Lange).

The polyesters manufactured by a process using the catalytic compositions of the invention are made by esterification and, optionally, subsequent polycondensation. These polyesters are especially suited for bottles, films, foils, yarn and/or molded padding, or resins for powder coatings or technical synthetic materials, Preferred polyesters according to the invention include:
a) polyethylene terephthalate (PET), containing 0.1-10 mass % diethylene glycol and 0-10 mass % of isophthalic acid, 2-hydroxy-isophthalic acid, p-hydroxyisophthalic acid, 2,6-naphthalenedicarboxylic acid and/or 1,4-cyclohexane dimethanol as co-monomer;
b) polyester for powder coatings mainly poly-2,2-dimethyl-propyl-1,3-terephthalate;
c) polypropylene terephthalate (PPT);
d) polyester polyols as for example polydiethyleneglycol terephthalate;
e) polybutylene terephthalates (PBT);
f) polynaphthalene terephthalates (PNT)
g) polyethylene naphthalate (PEN).

The following examples illustrate the invention further without, however, limiting the invention. Unless otherwise indicated, parts and percentages relate to the weight, as in the remainder of the description.

Further subjects of the invention are described by the claims and are in total part of the description of the present invention.

EXAMPLES

Example 1

List of Catalytically Acting Ti-Containing Compositions

Apparatus:

250 ml three necked round bottom flask, tap funnel, magnetic stirrer, water separator, rotary evaporator.

Starting Materials, Quantities:

| | | |
|---|---|---|
| monobutyltin oxide | 20.88 g | [0.10 mol] |
| bis(2-ethylhexyl) phosphate | 5.15 g | [0.016 mol] |
| 1a) without alcoholate | | |
| 1b) titanium tetrabutanolate | 4.25 g | [0.0125 mol] |
| 1c) sodium methanolate | 2.70 g | [0.05 mol] |
| 1d) aluminum triethoxide | 2.60 g | [0.016 mol] |
| 1e) aluminum tri(sec-butoxide) | 4.40 g | [0.016 mol] |
| 1f) aluminum tri(isopropoxide) | 3.39 g | [0.016 mol] |

Synthesis:

Monobutyltin oxide was suspended In xylene (150 ml), bis(2-ethylhexyl)phosphate was added within 10 min and the suspension is heated under reflux until the water formation stopped. After reaching room temperature the reaction was filtered. The metal alcoholate was added to the filtrate, which was then heated under reflux for an additional hour. The product was received after removal of the solvent under reduced pressure.

Further Alkyltin Catalysts:

Comparative Example 1g (Tributyltin (2-ethylhexanoate)

A three-necked flask equipped with mechanical mixer, heating, thermometer and vacuum distillation bridge was, under nitrogen protective atmosphere, filled with 149 (0.25 Mol) hexabutyidistannoxane and 72.1 g (0.5 Mol) 2-ethylhexanoic acid. The reaction mixture was heated up on 80° C. To separate from the reaction water a vacuum of 1 mbar was applied, and the reaction mixture was stirred another 1 h at this temperature.

Yield: 209.8 g (theoretical. 212.1 g) a clear, bright liquid. Elemental analysis: Sn content =27.8%.

The production of the examples and comparative examples 1 h to 1 n followed the same procedure.

Comparative example 1 h

Dibutyltin bis(2-ethylhexanoate)

Example 11

Monobutyltin tris(2-ethylhexanoate)

Comparative example 1J

Dibutyltin pinacolate

Example 1k

Monooctylstannoic acid

Example 1l

Monobutylstannoic acid

Example 1m

Monooctyltin tris(2-ethylhexanoate)

Example 1n

Monododecyltin tris(2-ethylhexanoate)

Example 2

Catalyst Test by Synthesis of a Resin for Powder Coatings

Starting Materials, Quantities:

| | | |
|---|---|---|
| terephthalic acid | 83.07 g | [0.50 mol] |
| neopentyl glycol | (2,2-dimethyl-1,3-propandiol) | |
| | 104.15 g | [1.00 mol] |
| catalyst: | 0.05% [m/m] (as metal) | |

Synthesis:

Catalyst, neopentyl glycol and terephthalic acid were given Into a 250 ml three necked round bottom flask. The mixture was heated to a maximum by the means of a heating mantel and the reaction water was distilled off and the amount was measured.

The reaction time equals the time between the first water formation and the "clear point" of the reaction.

Table 1 shows the acceleration of the reaction time In the described resin synthesis with the mixtures of examples 1a, 1b, 1c, 1d, 1e, 1f In comparison with the uncatalized reaction or with monobutyltin oxide (0.05% [m/m]) as catalyst.

TABLE 1

Reaction time of the mixtures a-f in comparison.

| Catalyst (0.05% as Sn) | Volume H₂O [ml]: | | | | | | | | | | | | [min] Reaction time | Remarks |
|---|---|---|---|---|---|---|---|---|---|---|---|---|---|---|
| | 15 min | 30 min | 45 min | 60 min | 75 min | 90 min | 105 min | 120 min | 135 min | 150 min | 165 min | 180 min | | |
| Without catalyst | | | | 1 | | 1 | | 2 | | 3 | | 4 | 300 | aborted |

TABLE 1-continued

Reaction time of the mixtures a-f in comparison.

| Catalyst (0.05% as Sn) | Volume $H_2O$ [ml]: | | | | | | | | | | | | [min] Reaction time | Remarks |
|---|---|---|---|---|---|---|---|---|---|---|---|---|---|---|
| | 15 min | 30 min | 45 min | 60 min | 75 min | 90 min | 105 min | 120 min | 135 min | 150 min | 165 min | 180 min | | |
| monobutyl-tinoxide | | 7 | | 9 | | 12 | | 15 | | 17 | | 19 | 180 | Clear, colorless |
| 1a | | 7 | | 10 | | 18 | | | | | | | 90 | Clear, colorless |
| 1b | 3 | 6 | 5 | 9 | 11 | 14 | | | | | | | 90 | Hazy, colorless |
| 1c | 4 | 4 | 10 | 14 | 16 | | | | | | | | 75 | Clear, colorless |
| 1d | 3 | 6 | 10 | 12 | 14 | 16 | | | | | | | 90 | Clear, colorless |
| e | 3 | 5 | 6 | 8 | 9 | 10 | 13 | 15 | 18 | | | | 135 | Clear, colorless |
| f | 3 | 5 | 7 | 10 | 12 | 14 | 15 | 16 | 18 | | | | 135 | Clear, colorless |

Example 3

Catalytically Active Sn-Compounds with A=Alcoholate

Example 3o

Product of the Reaction of Monobutyl Stannic Acid with TI(OBu)$_4$ (molar ratio, 4:1)

51.1 g (0.15 mol) TI(OBu)$_4$ and 25.3 9 (0.60 mol) monobutyl stannic acid were dissolved In xylene (250 ml) and refluxed under a nitrogen atmosphere In a 500 ml three necked round bottom flask for 4 hours. The product was obtained after the solvent was removed under reduced pressure in an amount of 149.6 g (theoretical. 131.9 g) as a yellow solid (Elemental analysis: Sn content=46.5%, Ti content=4.9%).

Example 3p

Product of the reaction of monooctyl stannic acid with Ti(OBU)$_4$ (molar ratio 1:1), synthesis in analogy to catalyst o.

Example 3q

Product from monooctylstannoic acid with tetrabutyl titanate (amount of substance ratio 4:1), synthesis In analogy to Example 3o.

Example 3r

Product from monobutylstannoic acid with tetrabutyl titanate (molar ratio 2:1), synthesis In analogy to Example 3o.

Example 4

Polycondensation of bis(2-hydroxyethyl)tereghthalate (BHET)

Experimental Method

Polycondensation equipment 1 (glass equipment) for the melt polycondensation of BHET Tempering-bath (salt bath), polycondensatlon vessel (glass), screw mixer (glass), vacuum pump, pressure gauge As a polycondensation equipment a round glass flask with round bottom was used, (internal diameter 2.6 cm, and 35 cm height, described in T. Johnson, Chem. Fibers International 46 (1996) 280; 49 (1999) 455). A horizontal vapor outlet Is integrated into the upper third of the flask wall. A further extension tube near the bottom of the vessel allowed sampling from the polymer melt. The stirrer was a glassware screw mixer, reaching down to the ground (1.8 cm diameters). The mixer was operated with a rotation speed of 100 min$^{-1}$ and Intermixed the melt with axially downward direction.

25.4 g (0.1 mol) BHET were filled into the polycondensation vessel, the catalyst (5 to 200 ppm as metal) was added and the vessel locked. Then the polycondensation vessel filled with the reaction mixture was evacuated three times and flushed with dry nitrogen before It was immersed In the tempering-bath. The bath temperature was preset so that the desired Internal temperature of 280° C. was reached in the polycondensation vessel. After the reaction mixture was melted, the stirrer was started and the vessel evacuated within 15 min onto a vacuum of 2×10$^{-1}$ mbar. The time of the first formation of glycol at the wall of the glass was regarded as $t_0$. The attainable final pressure for this equipment of approximately 4 to 5×10$^{-2}$ mbar, was reached after approx. 1 h experimental time, depending on the progress of the polycondensation. Through the sampling device samples could be taken by means of a VA steel wire, maintaining a nitrogen counter flow. At the end of the reaction up to 5 g could be taken from the vessel for further analysis. During the polycondensation, an average sampling required one minute, from breaking the vacuum to re-applying the vacuum. At the end of the polycondensation sampling was done within two minutes after aerating the vacuum.

PET Characterization

The determination of the intrinsic viscosities was performed as follows:

The relative solution viscosities $\eta_{rel}$, for PET were determined in phenol (3 parts)/dichlorobenzene (2 parts) mixtures using 0.5 percent solutions at 25° C. The conversion of the relative solution viscosities into the intrinsic viscosity [η] was done according to BILLMEIER.

$$\eta_{intr} = \frac{1}{4} \frac{\eta_{rel} - 1}{c + 3/4} \times \frac{\ln \eta_{rel}}{c}$$

From the intrinsic viscosities (IV) the average molecular weights Mn (number average) as well as the degrees of polymerization $P_n$ were calculated. For PET applies: Mn= $(1000 \times IV)^{1,5186}$; Pn=Mn/192.

The absolute viscosities were measured using the viscosimeter AVS 250 and the tempering-unit CT 1450 of Schott Geräte GmbH, Germany. Comparison measurements between different laboratories gave matching results.

The color values were determined using the CIE-LAB-Farbsystem (color system) by the spectral reference beam color measuring instrument LUCI 100, Dr. Lange.

The device STA 625 of Polymer Laboratories was used for TG and DSC-measurements.

The COOH end groups were determined by potentiometric titration of the in cresol solution of the polymers with diluted aqueous NaOH.

BHET and the catalyst were introduced Into the reaction vessel and rinsed well with nitrogen.

The reaction vessel was placed into the salt bath. Recording of reaction time started now. Within 15 min the pressure was lowered from 100 mbar to 0.09 mbar. At the end of the reaction a pressure of 0.04 mbar was reached.

The following table 2 shows the results of the polycondensation experiments for the catalysts of examples 1a, 3p and 3q in comparison to Sb- and Ti-based catalysts (table 3). Criteria for determining catalyst activity are the attainable molecular masses in specific time periods, the increasing influence of the thermal degradation, recognizable by the flattening of the $P_n$-t-function as well as the color values of the polyester. The amount of the evolved ethanal (acetaldehyde) that directly correlates with the degree of thermal ester group cleavage is a further essential criterion of the catalyst suitability. The color values In the tables show the discoloration of the product, the a-values representing green/red-gradients and the b-values representing blue/yellow-gradients. Negative a-values correspond to green, negative b-values correspond to blue gradients. Blue shift is favored technologically.

The comparative Investigations for the catalytic activity of the selected tin compounds show that no noteworthy thermal decomposition is to be expected within 2 h of polycondensatlon time at temperatures of 280° C. Therefore it is absolutely possible to synthesize even higher molecular weight polyethylene terephthalates by prolongation of the polycondensation time.

All examined tin compounds proved to be high-activity catalysts for the polycondensation of BHET which showed significantly higher activity than stiblous compounds. Their polytransesterification activity was superior to that of titanium alkoxides and titanium chelates. If required, they may alternatively be employed In higher concentrations.

TABLE 2

Polycondensation of BHET with the catalysts of examples 1a, 3p and 3q.

| catalyst of example | time [min] | molar ratio Ti/Sn | concentration Sn/Ti [ppm] | $M_n$ [g/mol] | $P_n$ | color values using the CIE-LAB-system L | a | b |
|---|---|---|---|---|---|---|---|---|
| 1a | 30 | 0/1 | 116 | 2090 | 9 | — | — | — |
| 1a | 60 | 0/1 | 116 | 3812 | 20 | — | — | — |
| 1a | 90 | 0/1 | 116 | 6145 | 32 | 33.01 | −0.05 | 1.18 |
| 1a | 120 | 0/1 | 116 | 16559 | 86 | 37.81 | −0.46 | 2.64 |
| 3p | 20 | 1:1 | 20/9 | 3839 | 20 | | | |
| 3p | 42 | 1:1 | 20/9 | 15454 | 80 | 67.15 | −0.21 | 1.30 |
| 3p | 96 | 1:1 | 20/9 | 25733 | 134 | 72.79 | −1.03 | 0.61 |
| 3p | 120 | 1:1 | 20/9 | 28454 | 148 | 68.06 | −1.06 | 2.76 |
| 3q | 15 | 1:4 | 20/2.25 | 1635 | 8 | | | |
| 3q | 31 | 1:4 | 20/2.25 | 4734 | 24 | 86.69 | −0.87 | −4.38 |
| 3q | 60 | 1:4 | 20/2.25 | 13499 | 70 | 70.38 | −0.38 | −0.31 |
| 3q | 90 | 1:4 | 20/2.25 | 18759 | 97 | 73.54 | −0.60 | 1.43 |

TABLE 3

Polycondensation of BHET with Sb and Ti catalysts.

| catalyst | temperature [° C.] | time [min] | catalyst conc. [ppm] | $P_n$ |
|---|---|---|---|---|
| antimony triacetate | 270 | 30 | 190 | 25 |
| antimony triacetate | 270 | 60 | 190 | 45 |
| antimony triacetate | 270 | 90 | 190 | 65 |
| antimony triacetate | 270 | 120 | 190 | 85 |
| antimony triacetate | 270 | 150 | 190 | 100 |
| antimony triacetate | 270 | 180 | 190 | 115 |
| antimony triacetate | 280 | 30 | 190 | 30 |
| antimony triacetate | 280 | 60 | 190 | 55 |
| antimony triacetate | 280 | 90 | 190 | 75 |
| antimony triacetate | 280 | 120 | 190 | 95 |
| antimony triacetate | 280 | 150 | 190 | 115 |
| antimony triacetate | 280 | 180 | 190 | 135 |
| tetrabutyl titanate | 280 | 30 | 20 | 45 |
| tetrabutyl titanate | 280 | 60 | 20 | 65 |
| tetrabutyl titanate | 280 | 90 | 20 | 85 |
| tetrabutyl titanate | 280 | 120 | 20 | 105 |
| tetrabutyl titanate | 280 | 150 | 20 | 125 |
| tetrabutyl titanate | 280 | 180 | 20 | 150 |

Further polycondensation reactions starting from bis-(2-hydroxyethyl)-terephthalate (BHET) were carried out in the glass equipment with screw mixer in presence of the catalysts 1 until 12.

Catalyst of comparative example 1g: tributyltin (2-ethylhexanoate)
Catalyst of comparative example 1h: dibutyltin bis(2-ethylhexanoate)
Catalyst of example 1f: monobutyltin tris (2-ethylhexanoate)
Catalyst of comparative example 1j: dibutyltin pinacolate
Catalyst of example 1k: monooctylstannoic acid
Catalyst of example 1l: monobutylstannoic acid
Catalyst of example 1m: monooctyltin tris(2-ethylhexanoate)
Catalyst of example 1n: monododecyltin tris(2-ethylhexanoate)
Catalyst of example 3o: conversion product from monobutylstannoic acid with tetrabutyl titanate (4 Mol: 1 Mol)
Catalyst of example 3p: conversion product from monooctylstannoic acid with tetrabutyl titanate (1 Mol: 1 Mol)
Catalyst of example 3q: conversion product from monooctylstannoic acid with tetrabutyl titanate (4 Mol: 1 Mol)
Catalyst of example 3r: conversion product from monobutylstannoic acid with tetrabutyl titanate (2 Mol: 1 Mol)

For the determination of the catalyst activity at first two concentrations of 20 ppm and 100 ppm were compared. The catalysts of (comparative) examples 1g through 1j were dissolved in toluene.

The catalysts were dissolved in dry toluene. The neat tin catalysts were used at a catalyst concentration of 40 ppm. The mixed catalysts (catalyst of examples 3o through 3q) were used at a tin content of 20 ppm. For the catalyst of example 3r the tin content of the catalyst was 22.9 ppm.

The tables 4a and 4b show the tin content and dosed catalyst amounts of the respective experiments.

BHET and the catalyst were introduced into the reaction vessel and rinsed well with nitrogen.

The reaction vessel was placed Into the salt bath. Recording of reaction time started now. Within 15 min the pressure was lowered from 100 mbar to 0.09 mbar. At the end of the reaction a pressure of 0.04 mbar was reached.

The results are shown in the tables 5 to 15.

The following tables show the results of the polycondensation experiments. Criteria of the catalyst activity are the attainable molecular masses In specific time periods, the increasing Influence of the thermal degradation, recognizable by the flattening of the $P_n$-t-function as well as the color values of the polyester. The amount of the evolved ethanal that directly correlates with the degree of thermal ester group cleavage is a further essential criterion of the catalyst suitability. The color values in the tables show the discoloration of the product, the a-values representing green/red-gradients and the b-values representing blue/yellow-gradients. Negative a-values correspond to green, negative b-values correspond to blue gradients. Blue shift is favored technologically.

The comparative Investigations for the catalytic activity of the selected tin compounds show that no noteworthy thermal decomposition is to be expected within 2 h of polycondensation. time at temperatures of 280° C. Therefore It is absolutely possibly to synthesize even higher molecular weight polyethylene terephthalates by prolongation of the polycondensation time.

All examined tin compounds proved as high-activity catalysts for the polycondensation of BHET which show significantly higher activity than stiblous compounds. Their polytransesterificatlon activity is superior to titanium alkoxides and titanium chelates. If required, they can be employed also In higher concentrations.

For the butyltin(2-ethylhexanoates) the activity sinks with increasing alkyl substitution. With regard to the achieved color values the monoalkyltin tricarboxylate are preferred to the di- and trialkyltin carboxylates.

TABLE 4a

Tin content and added catalyst amounts

| catalyst of example/ comparative example | tin content [%] | amount in 50 ml stock solution [mg] | catalyst in reaction mixture for 20 ppm Sn [mg] | catalyst in reaction mixture for 100 ppm Sn [mg] |
|---|---|---|---|---|
| 1g | 27.8 | 182.27 | 1.8227 | 9.137 |
| 1h | 22.9 | 221.8 | 2.218 | 11.09 |
| 1i | 20.0 | 254.0 | 2.54 | 12.7 |
| 1j | 35.1 | 144.7 | 1.447 | 7.24 |
| 1k | 44.0 | | | 5.780 |
| 1l | 56.0 | | | 4.535 |

TABLE 4b

Tin content and added catalyst amounts

| catalyst of example/ comp. example | tin content [%] | amount of catalyst in 50 ml stock solution [mg] | amount of catalyst in the reaction mixture [mg]/[ppm] Sn |
|---|---|---|---|
| 1m | 17.5 | 580.57 | 5.8/40 |
| 1n | 16.1 | 631.06 | 6.3/40 |
| 3o | 21.0 | 241.9 | 2.4/20 |
| 3p | 37.0 | 137.3 | 1.4/20 |
| 3q | 37.5 | 155.5 | 1.6/22.9 |
| 3r | 46.5 | 109.24 | 1.1/20 |

TABLE 5

Polycondensation of BHET in presence of the catalyst of comparative example 1g

| time [min] | concentration Sn [ppm] | $M_n$ [g/Mol] | $P_i$ | color values using the CIE-LAB-system | | |
|---|---|---|---|---|---|---|
| | | | | L | a | a |
| 15 | 100 | 3127 | 16 | 40.80 | −0.34 | −2.06 |
| 30 | 100 | 5953 | 31 | 36.15 | −0.22 | 0.04 |
| 60 | 100 | 13943 | 72 | 29.68 | −0.03 | 0.18 |
| 90 | 100 | 20281 | 105 | 30.04 | 0.04 | 0.52 |
| 120 | 100 | 23083 | 120 | 50.56 | −1.65 | 1.36 |
| 30 | 20 | 3046 | 16 | | | |
| 60 | 20 | 5972 | 31 | 40.3 | −0.64 | −3.51 |
| 90 | 20 | 9933 | 51 | 32.33 | −0.39 | −1.47 |
| 120 | 20 | 13356 | 69 | 47.88 | −0.49 | −0.20 |

TABLE 6

Polycondensation of BHET in presence of the catalyst of comparative example 1h

| time [min] | concentration Sn [ppm] | $M_n$ [g/Mol] | $P_n$ | color values using the CIE-LAB-system | | |
|---|---|---|---|---|---|---|
| | | | | L | a | a |
| 16 | 100 | 3563 | 18 | 111 | −2.89 | −12.29 |
| 30 | 100 | 8099 | 42 | 71.9 | −0.57 | −1.11 |
| 60 | 100 | 18585 | 96 | 73.3 | −0.48 | 0.17 |
| 90 | 100 | 22289 | 116 | 70.9 | −0.61 | 1.46 |
| 120 | 100 | 27090 | 141 | 74.4 | −0.71 | 1.94 |
| 30 | 20 | 5563 | 29 | 78.3 | −1.15 | −5.68 |

TABLE 6-continued

Polycondensation of BHET in presence of the catalyst of comparative example 1h

| time | concentration | $M_n$ | | color values using the CIE-LAB-system | | |
|---|---|---|---|---|---|---|
| [min] | Sn [ppm] | [g/Mol] | $P_n$ | L | a | a |
| 60 | 20 | 9172 | 47 | 70.3 | −0.34 | −1.13 |
| 90 | 20 | 13294 | 69 | 66.4 | −0.30 | 1.07 |
| 120 | 20 | 17636 | 92 | 72.1 | −0.3 | 0.0 |

TABLE 7

Polycondensation of BHET in presence of the catalyst of example 1i

| time | concentration | $M_n$ | | color values using the CIE-LAB-system | | |
|---|---|---|---|---|---|---|
| [min] | Sn [ppm] | [g/Mol] | $P_n$ | L | a | a |
| 15 | 100 | 4911 | 25 | | | |
| 30 | 100 | 10779 | 56 | 82.4 | −1.85 | 0.83 |
| 60 | 100 | 19581 | 102 | 71.7 | −1.14 | 3.94 |
| 90 | 100 | 25191 | 131 | 65.9 | −1.32 | 8.52 |
| 120 | 100 | 28701 | 149 | 69.5 | −1.11 | 7.69 |
| 30 | 20 | 6218 | 32 | | | |
| 60 | 20 | 11572 | 60 | 75.7 | −0.42 | −1.01 |
| 90 | 20 | 14656 | 76 | 68.8 | −0.16 | 0.57 |
| 120 | 20 | 19130 | 99 | 83.58 | −1.00 | −0.29 |

TABLE 8

Polycondensation of BHET in presence of the catalyst of comparative example 1j

| time | concentration | $M_n$ | | color values using the CIE-LAB-system | | |
|---|---|---|---|---|---|---|
| [min] | Sn [ppm] | [g/Mol] | $P_n$ | L | a | a |
| 15 | 100 | 1995 | 10 | | | |
| 30 | 100 | 3238 | 17 | | | |
| 60 | 100 | 14769 | 77 | 81.4 | −2.89 | −0.96 |
| 90 | 100 | 20684 | 107 | 71 | −1.21 | 4.13 |
| 120 | 100 | 24106 | 125 | 73.8 | −1.52 | 5.4 |

TABLE 9

Polycondensation of BHET in presence of the catalyst of example 1k

| time | concentration | $M_n$ | | color values using the CIE-LAB-system | | |
|---|---|---|---|---|---|---|
| [min] | Sn [ppm] | [g/Mol] | $P_n$ | L | a | b |
| 15 | 100 | 3066 | 16 | | | |
| 30 | 100 | 9071 | 47 | 70.9 | −0.49 | 0.68 |
| 60 | 100 | 18234 | 95 | 69.3 | −1.12 | 4.47 |
| 90 | 100 | 25817 | 134 | 82.5 | −1.65 | 13.4 |
| 120 | 100 | 27261 | 142 | 79.2 | −1.09 | 10.1 |

TABLE 10

Polycondensation of BHET in presence of the catalyst of example 1l

| time | concentration | $M_n$ | | color values using the CIE-LAB-system | | |
|---|---|---|---|---|---|---|
| [min] | Sn [ppm] | [g/Mol] | $P_n$ | L | a | b |
| 15 | 100 | 1932 | 10 | | | |
| 30 | 100 | 7241 | 37 | 111.2 | −4.7 | −4.84 |
| 60 | 100 | 16217 | 84 | 74.7 | −2 | 5.07 |
| 90 | 100 | 21936 | 114 | 70.3 | −1.2 | 6.28 |
| 120 | 100 | 24761 | 129 | 69.9 | −1.45 | 9.92 |

TABLE 11

Polycondensation of BHET in presence of the catalyst of example 1m

| time | concentration | $M_n$ | | color values using the CIE-LAB-system | | |
|---|---|---|---|---|---|---|
| [min] | Sn [ppm] | [g/Mol] | $P_n$ | L | a | b |
| 15 | 40 | 2437 | 12 | | | |
| 31 | 40 | 5494 | 28 | 81.07 | −1.86 | −7.12 |
| 45 | 40 | 8602 | 44 | 71.80 | −0.31 | −0.23 |
| 60 | 40 | 11282 | 58 | 71.52 | −0.40 | 0.40 |
| 90 | 40 | 16914 | 88 | 68.03 | −0.21 | 2.70 |
| 120 | 40 | 20107 | 104 | 75.86 | −0.83 | 2.51 |

TABLE 12

Polycondensation of BHET in presence of the catalyst of example 1n

| time | concentration | $M_n$ | | color values using the CIE-LAB-system | | |
|---|---|---|---|---|---|---|
| [min] | Sn [ppm] | [g/Mol] | $P_n$ | L | a | b |
| 20 | 40 | 3317 | 17 | | | |
| 40 | 40 | 7051 | 36 | 75.66 | −0.57 | −2.49 |
| 60 | 40 | 11588 | 60 | 72.37 | −0.50 | −0.63 |
| 90 | 40 | 16132 | 84 | 64.23 | −0.31 | 1.49 |
| 120 | 40 | 20633 | 107 | 69.23 | −0.66 | 1.68 |
| 160 | 40 | 24053 | 125 | 74.12 | −0.97 | 2.59 |

TABLE 13

Polycondensation of BHET in presence of the catalyst of example 3p and the catalyst of example 3q

| catalyst of example | time [min] | molar ratio Ti/Sn | concentration Sn/Ti [ppm] | $M_n$ [g/mol] | $P_n$ | color values using the CIE-LAB-system | | |
|---|---|---|---|---|---|---|---|---|
| | | | | | | L | a | b |
| 3p | 20 | 1:1 | 20/9 | 3839 | 20 | | | |
| 3p | 42 | 1:1 | 20/9 | 15454 | 80 | 67.15 | −0.21 | 1.30 |
| 3p | 96 | 1:1 | 20/9 | 25733 | 134 | 72.79 | −1.03 | 0.61 |
| 3p | 120 | 1:1 | 20/9 | 28454 | 148 | 68.06 | −1.06 | 2.76 |
| 3q | 15 | 1:4 | 20/2.25 | 1635 | 8 | | | |
| 3q | 31 | 1:4 | 20/2.25 | 4734 | 24 | 86.69 | −0.87 | −4.38 |
| 3q | 60 | 1:4 | 20/2.25 | 13499 | 70 | 70.38 | −0.38 | −0.31 |
| 3q | 90 | 1:4 | 20/2.25 | 18759 | 97 | 73.54 | −0.60 | 1.43 |
| 3q | 120 | 1:4 | 20/2.25 | 23273 | 121 | 71.45 | −0.77 | 1.09 |

TABLE 14

Polycondensation of BHET in presence of the catalyst of example 3r and the catalyst of example 3o

| catalyst of example | time [min] | molar ratio Ti/Sn | concentration Sn/Ti [ppm] | $M_n$ [g/mol] | $P_n$ | Color values using the CIE-LAB-system | | |
|---|---|---|---|---|---|---|---|---|
| | | | | | | L | a | b |
| 3r | 20 | 1:2 | 20/4.5 | 1259 | 6 | | | |
| 3r | 32 | 1:2 | 20/4.5 | 5043 | 26 | 111.81 | −2.42 | −4.93 |
| 3r | 60 | 1:2 | 20/4.5 | 15788 | 82 | 78.13 | −0.93 | 0.00 |
| 3r | 90 | 1:2 | 20/4.5 | 19198 | 100 | 69.56 | −0.83 | 1.88 |
| 3r | 120 | 1:2 | 20/4.5 | 23098 | 120 | 87.40 | −2.06 | 4.53 |
| 3r | 20 | 1:4 | 20/2.25 | 1687 | 8 | | | |
| 3r | 40 | 1:4 | 20/2.25 | 8181 | 42 | 71.67 | −0.16 | −0.64 |
| 3o | 60 | 1:4 | 20/2.25 | 14469 | 75 | 77.63 | −0.31 | −0.56 |
| 3o | 90 | 1:4 | 20/2.25 | 17388 | 90 | 82.78 | −0.63 | 1.21 |
| 3o | 120 | 1:4 | 20/2.25 | 24460 | 127 | 78.06 | −0.74 | 0.77 |

Catalytic activity depending on the structure of the tin compounds

TABLE 15

Effective rate constants of the polycondensation of BHET in presence of tin compounds and/or tin-titanium mixed compounds

| Catalyst of example/ [comparative example] | $k * 10^3$ [mmol/g sec] Sn 20 ppm resp. $4 * 10^{-5}$ mol/mol | $k * 10^3$ [mmol/g sec] Sn 40 ppm resp. $8 * 10^{-5}$ mol/mol | $k * 10^3$ [mmol/g sec] Sn 100 ppm resp. $2 * 10^{-4}$ mol/mol |
|---|---|---|---|
| 3p | 4.8 | | |
| 3r | 4.0 | | |
| 3q | 3.5 | | |
| 3o | 3.5 | | |
| 1l | 2.8 | 3.1 | 5.3 |
| 1k | | 3.4 | 4.4 |
| 1m | | 3.1 | |
| 1n | | 3.0 | |
| [1h] | 2.5 | | 4.4 |
| [1j] | | | 4.2 |
| 1i | | | 3.9 |
| [1g] | 1.7 | | 3.6 |

Example 5

Polycondensation Starting with Terephthalic Acid and Ethylene Glycol

Experimental Method

Polycondensatlon equipment 2 (15 l lab reactor of the Co. Juchheim, Germany) for the direct esterification and polycondensation of direct esterification products.

The equipment consisted of a stainless steel double jacket mixing tank reactor with 15 liters nominal volume and with conical bottom equipped with bottom discharge. The mixer was a double lever mixer, which fitted to the conical bottom, with speed control and torque measurement. A glide ring seal with ethylene glycol formed the mixer lock as a sealing-liquid. The preheating of the mixing tank reactor was performed through a liquid circulation heating. The control of the temperature of the heat carrier was performed through a high temperature controller depending on the preset temperature In the reactor Interior. At the lid of the reactor a feed hopper, gas dispersion tube, pressure gauge, thermometer (dipping tube), Inspection window, light, overflow valve, reflux condenser and a Liebig condenser were Installed next to the mixer. A pipe condenser and a condensate receiver were downstream to the reflux condenser, the Liebig condenser ended in a second condensate receiver. The condensate receiver had gassing/degassing valves, pressure gauge, overflow valve as well as a vacuum equipment at the lid next to the feeding means.

For the generation of the primary vacuum of approx. 20 mbar a membrane pump was used and a rotary valve vacuum pump was used up to the final vacuum. The pressure control was done by means of vacuum controller in connection with a magnetic valve in front of the sucking-nozzle of the pump. The exits of the condensate receiver were combined at the pressure point of measurement and connected through two cold traps switched in series and filled with liquid nitrogen.

By means of data printer following measuring data could be registered continuously:

temperature at the lower inside wall in the reactor temperature in the melt (dipping tube in the lid)

reflux condenser head temperature reactor internal pressure torque at the mixer shaft Esterification, prepolycondensation and polycondensation were carried out in one experimental step. 20 mol terephthalic acid (TPA) were premixed intensely with 28 mol ethylene glycol (EG) until homogeneous. To this mixture the tin based catalysts were added. This mixture was filled into the reactor having been flushed with nitrogen before. The reactor was shut (time $t_0$), a mixer rotation speed set to 60 min$^{-1}$ and heated up to 230 to 240° C. internal temperature. The temperature rise was followed by an increase of pressure up to approx. 4.5 bar. The generated water was distilled off via the reflux condenser, which was tempered at 115° C. The head temperature in this case was kept between 170 and 190° C.

The end of the esterification (time $t_1$) was indicated by a drop of the head temperature and the internal pressure. For the catalyst dosing the esterification product was cooled to approx. 180° C. for a short moment. Then primary vacuum was applied and the reactor heated up to an internal temperature of 270 to 275° C. Upon reaching the primary vacuum (approx. 20 mbar) the rotary valve vacuum pump was started. At a final pressure <0.1 mbar the polycondensation started (time $t_2$), recognizable by the Increasing torque. With high melt viscosities it was necessary to reduce the mixer rotation speed since the mixer shaft was equipped with a shear-pen with a 60 Nm upper limit to protect the shaft. At the end of the polycondensation (time $t_3$) the mixer was disconnected and the evacuated vessel was flushed with nitrogen. The product was discharged from the reactor by the bottom discharge under nitrogen pressure. It was either poured onto a steel sheet to cool down in pellets, or the melt was led through a water bath, granulated and the product dried subsequently.

The material was dried in a vacuum oven at 130° C. for 6 h, then examined with respect to the Intrinsic viscosities, and the color values were determined as described before.

The polycondensation starting out from terephthalic acid and ethylene glycol were carried out in presence of the catalysts of examples 1l, 1n, and 3p.

Test conditions and results are shown in tables 16a and 16b.

TABLE 16a

Test conditions and polycondensation experiment in the 15l mixing tank reactor

| example | catalyst of example | T [° C.] | concentration [ppm] | esterification time [min] | polycondensation time [min] | intrinsic viscosity |
|---|---|---|---|---|---|---|
| 5a | 1i | 275 | 53 Sn | 180 | 105 | 0.85 |
| 5b | 1i | 275 | 26.5 Sn | 180 | 180 | 0.87 |
| 5c | 1l | 270 | 53 Sn | 165 | 170 | 0.90 |
| 5d | 1n | 270 | 53 Sn | 160 | 203 | 0.80 |
| 5e | 3p | 270 | 26.5 Sn + 12 Ti | 135 | 110 | 0.92 |

TABLE 16b

Results of the polycondensation experiment in the 15l mixing tank reactor

| example | $M_n$ [g/Mol] | Content of end groups × $10^6$ [mol/g] | Content of COOH × $10^6$ [mol/g] | Color value L | Color value a | Color value b | Amount of ethanal [ppm] |
|---|---|---|---|---|---|---|---|
| 5a | 28200 | 79.9 | 24.5 | 59.02 | −1.19 | −3.21 | 24 |
| 5b | 29300 | 68.6 | 28 | 72.04 | −2.08 | 0.28 | 15 |
| 5c | 30700 | 65.1 | 25 | 70.53 | −2.10 | −1.20 | 28 |
| 5d | 25600 | 82.3 | 23.5 | 58.14 | −0.47 | 0.79 | 20 |
| 5e | 31800 | 62.9 | 17 | 78.03 | −2.62 | 1.17 | 16 |

The invention claimed is:

1. A catalytic composition for esterification, transesterification and polycondensation reactions of dicarboxylic acids, polycarboxylic acids and/or hydroxy carboxylic acids and alcohols, said catalytic composition containing a tin compound of the general formula (I):

$$[(R^1Sn)_l(OH)_{m-n}(OR^2)_nO_o]^{p+} A^{q-}_{p/q} \quad \text{(formula I)}$$

wherein:
R$^1$ and R$^2$ each independently is a linear, branched or cyclic alkyl group or aryl group having 1 to 12 carbon atoms,
A$^{q-}$ is an anion,
l=12,
m=6,
n=1 to 6,
o=14,
p=2 and
q=1 to 2.

2. The catalytic composition according to claim 1, wherein the anion A$^{q-}$ is O$^{2-}$, OH$^-$, a linear, branched or cyclic alkyl carboxy group, aryl carboxy group or alkoxy group each having 1 to 12 carbon atoms, the anion of a mineral acid or a metalate.

3. The catalytic composition according to claim 2, wherein the anion A$^{q-}$ is a sulphate, sulphite, phosphate, halogenide or pseudo-halogenide, titanate, zirconate, aluminate or zincate anion.

4. The catalytic composition according to claim 1, wherein the anion A$^{q-}$ is a chloride anion and R$^1$ is an octyl- and/or butyl group.

5. A process for the preparation of a catalytic composition according to claim 1, said process comprising the step of reacting a metal alkoxide with a tin compound of the general formula:

$$[(R^1Sn)_l(OH)_mO_o]^{p+} A^{q-}_{p/q}.$$

6. The process according to claim 5, wherein said metal alkoxide and said tin compound are reacted in a mole proportion of 1:0.0001 up to 1:20, in particular 1:4 to 1:6, respectively.

7. The process according to claim 6, wherein resultant metal oxides, metal hydroxides and/or alkoxy metal hydroxides remain in the catalytic composition.

8. The process according to claim 5, wherein resultant metal oxides, metal hydroxides and/or alkoxy metal hydroxides remain in the catalytic composition.

9. A method for the continuous or batchwise production of esters or polycondensation products by esterification, transesterification, polyesterification or polytransesterification reaction, said method comprising using the catalytic composition as defined in claim 1.

10. The method according to claim 9, comprising a polyesterification reaction of a dicarboxylic acid derivative with a mono, divalent or polyvalent alcohol in the presence of the catalytic composition.

11. The method according to claim 10, employing derivatives of di or polycarboxylic acids selected from the group of esters or halogenides.

12. The method according to claim 9, employing derivatives of di or polycarboxylic acids selected from the group of esters or halogenides.

13. The method according to claim 9, employing derivatives of hydroxycarboxylic acids selected from esters.

14. The method according to claim 9, employing a metal concentration of said catalytic composition in the range of 0.1 ppm to 1 mole percent, in particular 10-100 ppm with reference to the acid or derivative to be reacted.

15. The method according to claim 9, employing a solvent or suspending agent for the manufacturing of the catalytic composition and/or said esterification, transesterification, polyesterification or polytransesterification reaction.

16. The method according to claim 15, employing the same solvent and/or suspending agent in the manufacturing of said catalytic composition and said esterification, transesterification, polyesterification or polytransesterification reaction.

17. The method according to claim 15, employing a solvent or suspending agent selected from the group consisting of mono-, di- or polyvalent alcohols being reacted in said esterification, transesterification, polyesterification or polytransesterification reaction.

* * * * *